United States Patent [19]
Stewart et al.

[11] Patent Number: 6,045,227
[45] Date of Patent: Apr. 4, 2000

[54] MULTI-FUNCTIONAL VISUAL TESTING INSTRUMENT

[75] Inventors: Jeffrey L. Stewart, Greenwich, Conn.; Robert K. Maloney, Los Angeles, Calif.

[73] Assignee: VisionRX.Com, Inc., Elmsford, N.Y.

[21] Appl. No.: 09/146,655

[22] Filed: Sep. 3, 1998

[51] Int. Cl.[7] ..................................................... A61B 3/02
[52] U.S. Cl. .............................................................. 351/237
[58] Field of Search .................................... 351/200, 222, 351/223, 226, 230, 231, 233, 237, 224, 243

[56] References Cited

U.S. PATENT DOCUMENTS

| | | | |
|---|---|---|---|
| 5,550,602 | 8/1996 | Braeuning | 351/243 |
| 5,617,157 | 4/1997 | Shalon et al. | 351/222 |
| 5,627,612 | 5/1997 | Hayashi | 351/200 |
| 5,864,384 | 1/1999 | McClure et al. | 351/224 |

*Primary Examiner*—George Manuel
*Attorney, Agent, or Firm*—John De La Rosa

[57] ABSTRACT

The present multi-functional, visual test instrument is realized by integrating miniature, close-proximity displays, such as LCDs, with viewing optics, which is constructed in the form of preferably a unitary housing. In a preferred embodiment, the multi-functional, visual test instrument includes two viewing assemblies, and displays, which are all enclosed in the housing that is slidably or pivotally attached to a movable mount, such as a slit lamp base. In operation, various optical test objects or stimuli are viewed by the patient on the displays through the viewing assemblies. The shape, size, speed, frequency, location, color, contrast and intensity of the test objects or stimuli are computer generated. A hand operated switch, mouse, joystick, or other input means, may be used for the patient to respond to the observed test objects or stimuli.

29 Claims, 4 Drawing Sheets

MULTI-FUNCTIONAL VISUAL TESTING INSTRUMENT

TECHNICAL FIELD

The present invention relates to a multi-functional instrument for testing the visual functions of a patient's eye, including perimetry, visual acuity, color discrimination, contrast sensitivity, and depth perception, among others.

BACKGROUND OF THE INVENTION

Visual function testing is performed to identify and analyze diseases and defects of the cornea, lens, retina, visual neural pathways, and other parts of the eye and vision system. Recently, so-called total immersion, "virtual reality" instruments have been used, for example, to display optical test objects or images to the patient for testing various visual functions of the eye. Generally, such instruments reduce patient fatigue as well as reduce the expense of the instrument. See, for example, U.S. Pat. Nos. 5,550,602 and 5,737,060, which are incorporated herein by reference.

Various types of displays have been used in "virtual reality" instruments, which include the use of large displays, or small, close-proximity displays. Unfortunately, large displays are generally too bulky and/or costly for general use. More recently, however, relatively small, close-proximity displays, such as CRTs or LCDs, have been employed in head-worn units, such as goggles, eyeglasses, and helmets, to display the appropriate visual test objects or stimuli to the patient. In such instruments, suitable optics is housed in the head-worn or head-mounted unit through which the visual test objects are viewed, so as to reduce bulk and/or increase portability.

Unfortunately, some patients have serious hygiene concerns regarding having to share a head-worn or head-mounted instrument, fearing, for example, catching head lice. Others, simply do not like or object to, for vanity reasons, using such visual test instruments, which can disturb their hair.

Accordingly, it is desirable in the art to provide for a multi-functional, close-proximity, total immersion, visual test instrument without the associated problems of the prior art.

SUMMARY OF THE INVENTION

The present total immersion, visual test instrument is realized by integrating miniature, close-proximity displays, such as LCDs, with viewing optics, which is preferably constructed in the form of a unitary housing. The unitary housing is designed to be snug fitting to the patient's face in order to exclude extraneous light, allowing testing to be performed under ordinary room light conditions.

In a preferred embodiment, the multi-functional, visual test instrument includes two viewing assemblies, and two displays, which are all enclosed in the unitary housing that is slidably or pivotally attached to a movable mount, such as a slit lamp base, or a spring loaded arm. Alternatively, the housing may be pivotally or slidably mounted to a post, pole, floor stand, instrument stand, table, or hand held. In this manner, the patient need not have concerns regarding having to share head-mounted or head-worn instruments.

In operation, various test objects or stimuli are viewed by the patient on the displays through the two viewing assemblies. The shape, size, speed, frequency, location, color, contrast and intensity, among others, of the test objects or stimuli are computer generated. Accordingly, the visual test instrument preferably includes a computer provided with a collection of software programs for directing the operation of the visual test instrument, conducting the test, storing the results, evaluating the responses of the patient to the observed test objects or stimuli, printing the results, and allowing the examiner to observe, when necessary, the test on the computer's monitor. A hand-operated switch, mouse or joystick, may be used for the patient to respond to the observed test objects or stimuli. Alternatively, a keyboard may be used. Additionally, voice recognition may be used, and audible instructions given to the patient to facilitate testing.

BRIEF DESCRIPTION OF THE DRAWINGS

The features and advantages of the present invention will become more readily apparent from the following detailed description of the invention in which like elements are labeled similarly and in which.

DETAILED DESCRIPTION

The present close-proximity, total immersion, visual test instrument is realized by integrating miniature, close-proximity displays with viewing optics, which is constructed preferably in the form of a unitary housing. Such close-proximity displays include CRTs, LCDs, plasma displays and the like, having a resolution at least sufficient to perform the desired visual test. Also, although color displays are preferable, it is contemplated that both black and white as well as color images may be displayed to the patient. Also, well-known fixation techniques may be used to maintain the patient's gaze at a predetermined point during examination, such as during perimetry.

Importantly, the housing is attached to a movable or positioning mount or so as to readily position the instrument relative to the patient's eyes. In this manner, the patient need not have hygiene concerns regarding having to share head-mounted or head-worn instruments. Also, such patients are unlikely to object to using the movably attached, visual test instrument of the present invention for vanity reasons since it is less likely to disturb their hair. This is so inasmuch as the weight of the instrument is not supported by, nor is any portion of the instrument wrapped around, the patient's head.

It is contemplated that the present invention performs comparable or the same visual tests as prior art, multi-functional, test instruments that are head-mounted or head-worn by patients, but without the associated problems of such prior art instruments. Such visual tests, include, perimetry, noise field campimetry, color discrimination, depth perception, visual acuity, near vision, contrast sensitivity and mesoptometry, among others, which are all well known in the art. Exemplary multi-functional, visual test instruments are disclosed, for example, in U.S. Pat. Nos. 4,869,589, 5,550,602, and 5,737,060, which are incorporated herein by reference.

Without any loss of generality or applicability for the principles of the present invention, the embodiment of the present invention is directed to a binocular construction wherein the optical portion consists of two halves, each substantially symmetrical with respect to a center line. It should, however, be clearly understood that the present multi-functional, visual test instrument is equally applicable to a monocular construction wherein only one of the two optical halves is contained in the housing of the visual test instrument.

Figure 1:
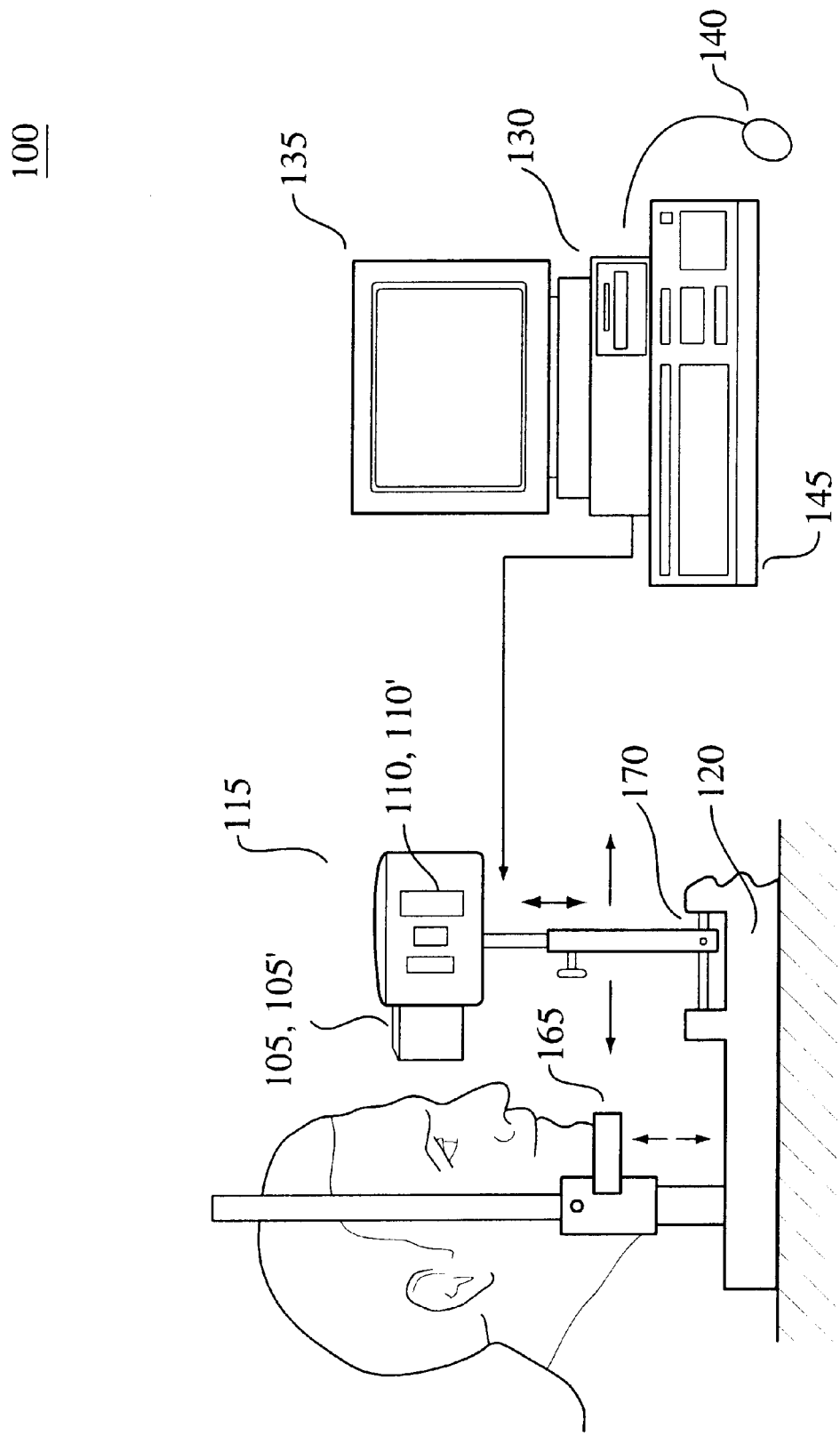
FIG. 1 is a perspective view of an embodiment of the multi-functional, visual test instrument of the present invention.
Figure 2:
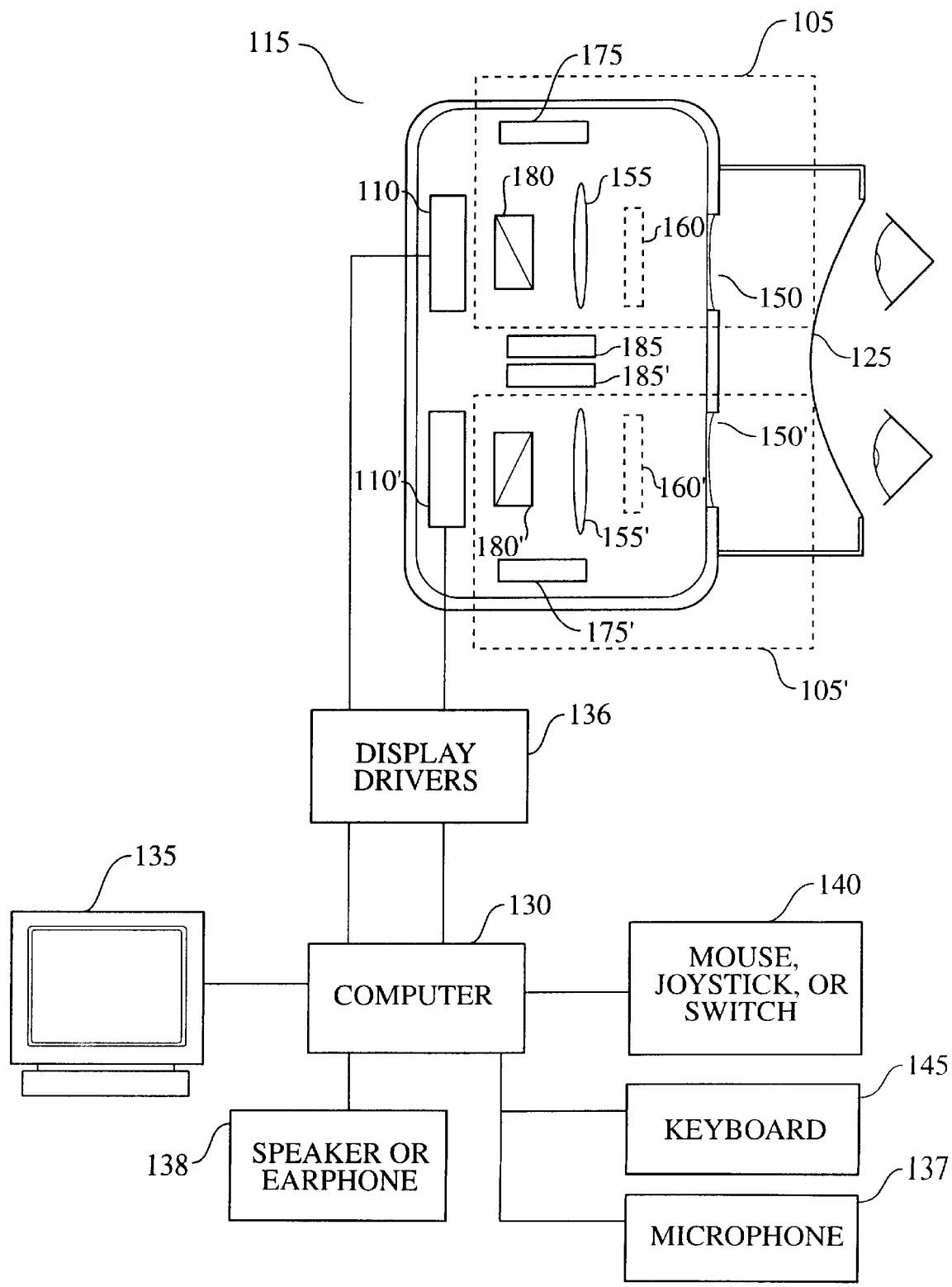
FIG. 2 is a schematic block diagram of the multi-functional, visual test instrument of FIG. 1.

Referring to FIGS. 1–2, there is shown an exemplary embodiment of a multi-functional, close proximity, total immersion, visual test instrument 100 in accordance with the principles of the invention. Multi-functional, visual test instrument 100 includes viewing assemblies 105,105', and displays 110,110', which are all enclosed, for example, in a housing 115 that is slidably or pivotally attached to a movable or positioning mount 120, such as a slit lamp base. Alternatively, housing 115 may be pivotally or slidably mounted to a post, pole, floor stand, instrument stand, table or hand held, as discussed herein below. It should be understood that mount 120 is specifically provided for properly positioning the visual test instrument relative to the patient's eyes.

In operation, various test objects or stimuli are viewed by the patient on displays 110,110' through viewing assemblies 105,105'. Viewing assemblies 105,105' may be slidably movable so as to be spaced apart from each other to permit the adjustment of the spacing between the pupils of the patient. Typically, the interpupillary distance ranges between about 56–72 mm. If desired, viewing assemblies 105,105' may be covered with eye shield 125, which may be disposable such as for single use purposes. The shape, size, speed, frequency, location, color, contrast and intensity, among others, of the test objects or stimuli are computer generated and controlled in a manner well known in the art, depending on the desired visual testing being performed on the patient. See, for example, U.S. Pat. Nos. 4,869,589, and 5,550,602 which are incorporated herein by reference.

Accordingly, visual test instrument 100 preferably includes a computer 130 provided with a collection of software programs for directing the operation of the visual test instrument, providing visual and audible feedback to the patient, conducting the test and evaluating the responses of the patient to the observed test objects and stimuli, storing and printing the results, and allowing the examiner to monitor the test on computer monitor 135, when necessary. Preferably, the software allows a clinician to preprogram a predetermined sequence of visual tests to be performed automatically on the patient, such as through the use of corresponding macro commands. When appropriate, various test objects or images are generated and presented on displays 105,105' using suitable electronics, such as display drivers 136. Thus, computer 130 provides the necessary visual signals and stimuli for the patient and then receives the feedback response necessary to effect visual testing. A hand-operated switch, mouse, joystick 140, or other input means, may be used for the patient to respond to the observed test objects or stimuli. Alternatively, a keyboard 145 may be used. If desired, visual test instrument 100 may also be provided with a microphone 137 and a speaker or earphone 138 for audio communication and feedback to computer 130 so as to effect the use of voice recognition and/or audible instructions.

For example, for testing for visual acuity, test objects of different sizes and shapes may be displayed to the patient. Either the clinician or the computer may then compare what the patient reports seeing with what is presented by computer 130 on monitor 135. The ability to differentiate between colors can be tested in a similar manner.

Preferably, viewing assemblies 105,105' are provided with suitable optics therein for viewing the computer generated test objects or stimuli in stereo wherein the two displays appear as a single display to the patient. This may be effected by presenting the displays along two different views in a manner similar to a conventional binocular, with the angle therebetween chosen for the best stereopsis. Such suitable optics may include, for example, the use of ocular lenses 150,150' and field lenses 155,155', which in combination magnify displays 110,110', respectively. Furthermore, such ocular lenses may be used to adjust the instrument's field of view as well as its depth of focus, among other things. Various types of ocular lenses may be used, such as, Hugens, Ramdsden, Kelner, Plossl, or Erfle eyepieces, among others, which are all well known in the art. Typically, virtual images of the displays, as well as of the optical test objects displayed thereon, are formed at a predetermined distance from the patient's eye. For certain visual tests, it is preferable that this latter distance is at or near infinity so that the visual test objects can be conformably viewed by a normal relaxed eye. For others visual tests, it may be preferable that the test objects appear nearer to the patient's eyes. The entrance pupil of the present visual instrument should, however, be large so as to accommodate varying interpupillary distances.

If desired, ocular eyepieces 150,150' may be movable a few millimeters along the optical axis of the instrument, such as by rotating a collar (not shown), so as to compensate for ametropia in the patient. Alternatively, a corrective lens may be attached to the front of each eyepiece to compensate for the patient's vision. Optionally, optical filters 160,160' may be positioned between displays 110,110' and ocular eyepieces 140,140', respectively, so as to tailor the spectral characteristics of the light from displays 110,110'.

In the above preferred embodiment, visual test instrument 100 is movably mounted on base 120 so that housing 115 may be brought to the patient while the patient maintains a comfortable position. Preferably, housing 115 is constructed to be snug fitting to the patient's face in order to exclude extraneous light, allowing testing to be performed under ordinary room light conditions. During examination, the patient's chin rests on a chin rest 165, with housing 115 then accordingly positioned so that the optical axis of the instrument is aligned with the patient's eyes. Positioning is effected by raising or lowering chin rest 160 as well as by raising or lowering the instrument. Positioning may also be effected by manipulating and using a slide 170 to move housing 115 forward and backward, and from side-to-side. Of course, a slit lamp base may be used instead of base 120. For a detailed description on the adjustment mechanism of a slit lamp base, see, for example, U.S. Pat. No. 3,463,579, which is incorporated herein reference.

Advantageously, visual test instrument 100 uses two displays, allowing both eyes to be tested at once. This is accomplished by generating the visual test objects and sending them to each of the two displays independently. In this manner, both eyes can also be used for fixation. If one eye has a defect in the central vision, its field of vision can still be tested because the other eye can still be used for fixation. For example, a test object can be first displayed on the right display of the visual test instrument, and then displayed at some time later on the left display, without the patient being able to distinguish which eye is being tested. In this latter manner, fixation may also be displayed independently to each eye, which fixation can be displayed at different locations on the display so as to increase the effective viewing area as well as to keep the patient's attention. Additionally, since it is unnecessary to patch one eye, it is more comfortable for the patient.

For examining the visual field of the patient, such as through perimetry, visual test instrument 100, for example, displays an optical fixation mark to the patient on displays 110,110'. Those skilled in the art will readily note that the fixation mark is a reference point or mark for other test objects to be displayed on the displays. Then, while the patient fixes his eye on the fixation point, test objects or marks are displayed of varying locations, color, brightness, contrast, and frequency, among others, with the patient then triggering a signal upon observing the marks at the varying locations, such as through the use of push-button switch, mouse or joystick 140, among others. Alternatively, voice recognition may be used. Specific fixation techniques that may be used include those disclosed in U.S. Pat. Nos. 4,995,717, 5,035,500, 5,565,949, and 5,737,0650, which are incorporated herein by reference.

For examining strabismus, as well as for other testing requiring eye tracking, eye-trackers 175,175' may be used. In this latter case, eye-trackers 175,175', preferably incorporating video cameras, may be arranged towards the side of viewing assemblies 105,105' so as to capture the image position of the patient's eyes through light reflected by beamsplitters 180,180' into the respective eye-trackers. Such an eye tracking system also allows the strabismal angle to be determined.

Still further, it is contemplated that light sensors 185,185' may be used to measure the brightness of displays 110,110' or the interior of housing 115, and then an appropriate feedback signal transmitted to computer 130, which accordingly adjusts the brightness of each display to a predetermined level.

Figure 3:
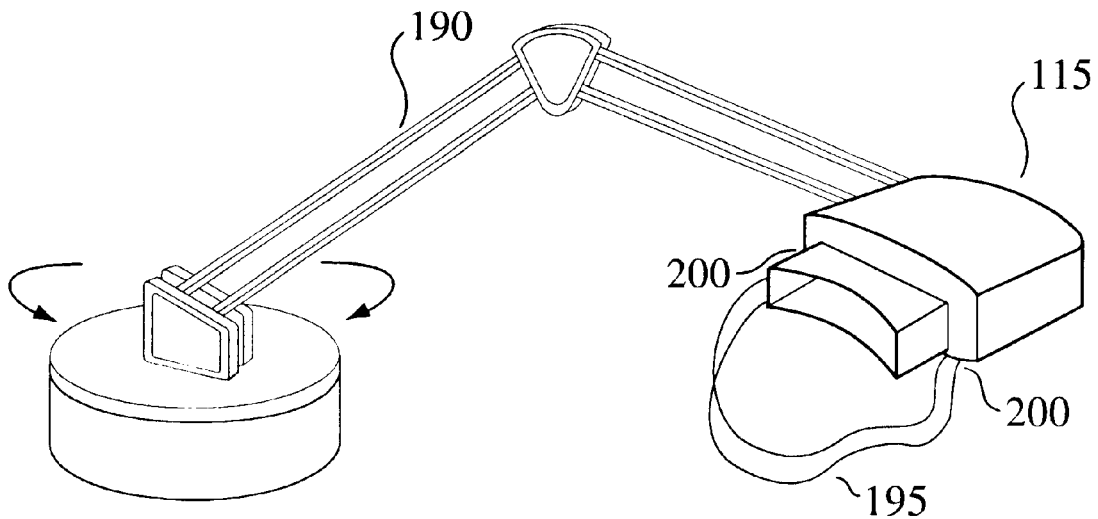
FIGS. 3–5 are perspective views of still other embodiments of the multi-functional, visual test instrument of the present invention.

Referring to FIG. 3, shown there is another embodiment of the present invention. Visual test instrument 100 is movably mounted to a spring loaded arm 190 so that housing 115 may be brought to the patient while the patient maintains a comfortable position. Alternatively, a goose neck arm may be used. In these latter embodiments, the visual test instrument may include a head strap 195, made, for example, of suitably sized material, such as nylon, paper or Tyvek, and adapted to fit around the head of the patient to keep housing 115 substantially fixed or immobile relative to the patient's eyes. It is contemplated that head strap 195 may be reusable or constructed for single use. Head strap 195 may be secured to the forward, top portion of housing 115 by coupling attachment means 200, such as adhesives or Velcro, or any other suitable means. In this manner, head-strap 195 may be readily removed and replaced after each use, if desired. Although head strap 195 is of sufficient strength to keep the instrument immobile relative to the patient's head, it is generally incapable of fully supporting the weight of the visual test instrument.

Figure 4:
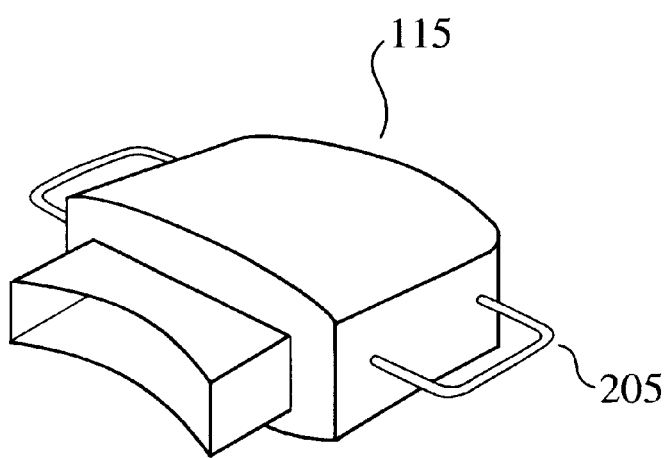

Alternatively, housing 115 may be adapted with a hand strap(s) or handle(s) 205 so that it can be hand held during examination, as illustrated in FIG. 4.

Figure 5:
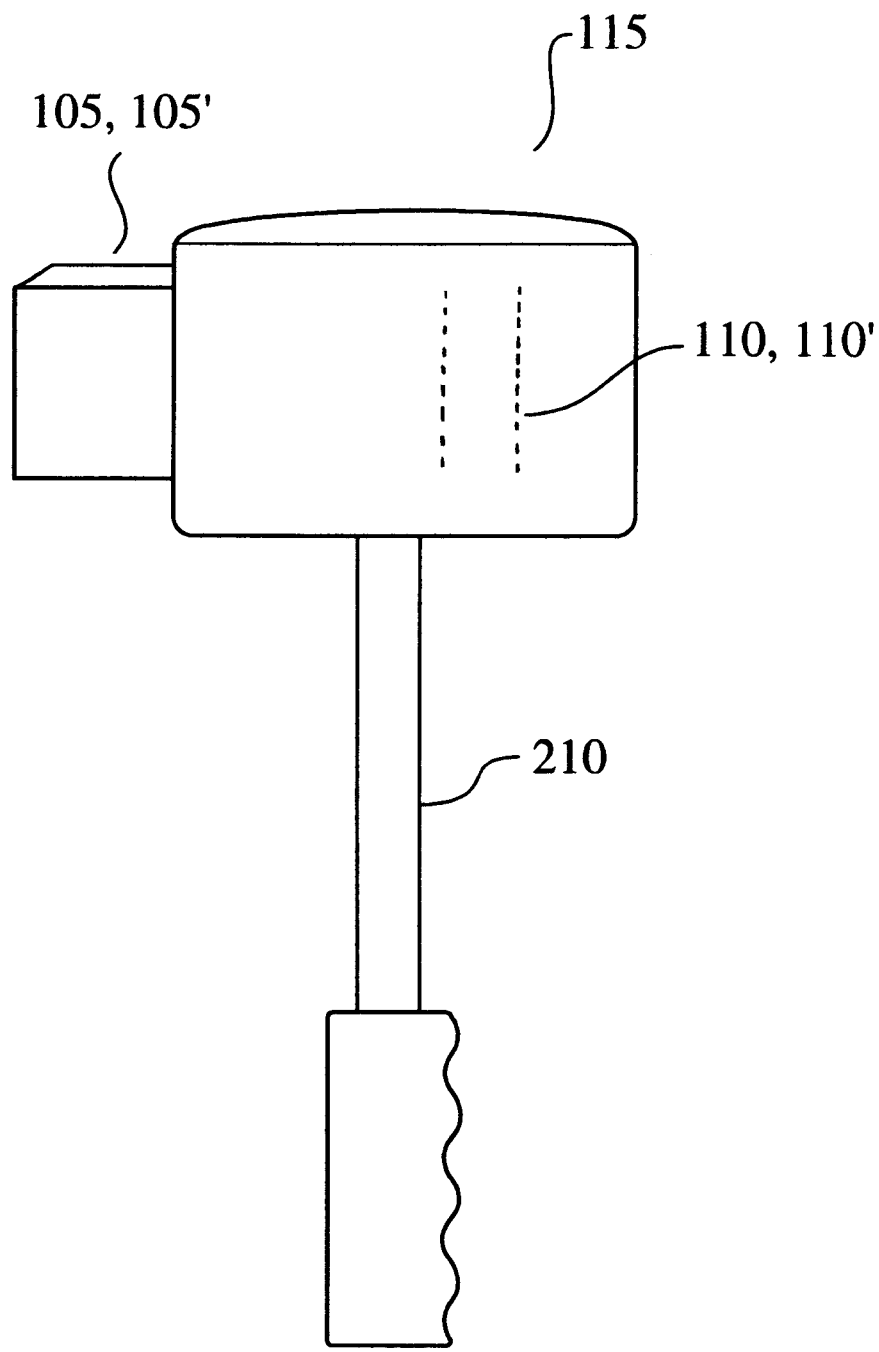

In still another alternative embodiment of the present invention, housing 115 may be adapted to be mounted on a hand held post 210, as illustrated in FIG. 5. In this latter embodiment, housing 115 may be provided with suitable threads within in a small opening in the underside of the housing of the visual test instrument. Corresponding threads within, for example, the front end of post 210 allows housing 115 to be screwed thereto. In this manner, visual test instrument 100 may be likewise readily hand held during testing.

It should be understood that the embodiments herein are merely illustrative of the principles of the invention. Various modifications may be made by those skilled in the art which will embody the principles of the invention and fall within the spirit and the scope thereof.

We claim:

1. A multi-functional visual test instrument comprising:
   (a) a housing adapted for positioning entirely in front of the patient's eyes and adapted to be snug fitting against the patient's face, said housing enclosing,
      (i) means for displaying visual test objects of varying size, speed, location, frequency, contrast, intensity, shape or color; and
      (ii) optical means through which the visual test objects are viewed by a patient; and
   (b) a mount, said housing movably attached to said mount for positioning said optical means near the patient's eye.

2. The visual test instrument of claim 1 wherein said means for displaying includes a LCD.

3. The visual test instrument of claim 1 wherein said mount includes a slit lamp base.

4. The visual test instrument of claim 1 wherein said mount includes a spring loaded arm.

5. The visual test instrument of claim 1 wherein said mount includes a chin rest.

6. The visual test instrument of claim 1 further comprising a computer for controlling the display of the visual test objects.

7. The visual test instrument of claim 1 wherein said optical means includes an adjustable ocular eyepiece.

8. The visual test instrument of claim 1 further comprising a head strap attached to said housing for keeping the patient's head fixed relative to said housing.

9. The visual test instrument of claim 1 wherein said means for displaying includes two displays, said visual test objects displayed on each display independently.

10. The visual test instrument of claim 1 further comprising an eye tracking system.

11. The visual test instrument of claim 1 further comprising a sensor for measuring the brightness of said means for displaying.

12. The visual instrument of claim 1 further comprising an eye shield for blocking out ambient light to the patient's eyes.

13. A multi-functional visual test instrument comprising:
   first and second displays;
   a computer for generating visual test objects of different size, location, speed, frequency, contrast, intensity, shape or color on said first and second displays;
   first and second optical means for viewing said visual test objects on said first and second displays, respectively;
   a housing adapted for positioning entirely in front of the patient's eyes and adapted to be snug fitting against the patient's face, said housing enclosing said first and second displays, and said first and second optical means; and
   a mount operatively attached to said housing for positioning said first and second optical means relative to a patient's eyes.

14. The visual test instrument of claim 13 wherein said housing is slidably attached to said mount.

15. The visual test instrument of claim 13 wherein said first and second displays are LCDs.

16. The visual test instrument of claim 13 wherein said mount includes a slit lamp base.

17. The visual test instrument of claim 13 wherein said mount includes a chin rest.

18. The visual test instrument of claim 13 wherein said first and second optical means include adjustable ocular eyepieces.

19. The visual test instrument of claim 13 further comprising a head strap attached to said housing for keeping the patient's head fixed relative to said housing.

20. The visual test instrument of claim 13 further comprising an eye tracking system.

21. The visual test instrument of claim 13 further comprising a sensor for measuring the brightness of said first and second displays.

22. The visual test instrument of claim 13 further comprising an eye shield for blocking out ambient light to the patient's eyes.

23. A multi-functional visual test instrument comprising:
(a) a housing adapted for positioning entirely in front of the patient's eyes and adapted to be snug fitting against the patient's face, said housing enclosing,
   (i) means for displaying visual test objects of varying size, location, speed, frequency, contrast, intensity, shape or color; and
   (ii) optical means through which the visual test objects are viewed by a patient; and
(b) a handle attached to said housing for positioning said optical means near the patient's eye.

24. The visual test instrument of claim 23 wherein said means for displaying includes a LCD.

25. The visual test instrument of claim 23 wherein said optical means includes an adjustable ocular eyepiece.

26. The visual test instrument of claim 23 wherein said means for displaying includes two displays, said visual test objects displayed on each display independently.

27. The visual test instrument of claim 23 further comprising an eye tracking system.

28. The visual test instrument of claim 23 further comprising a sensor for measuring the brightness of said means for displaying.

29. The visual test instrument of claim 23 further comprising an eye shield for blocking out ambient light to the patient's eyes.

* * * * *